United States Patent
Gao et al.

(10) Patent No.: US 7,576,250 B2
(45) Date of Patent: Aug. 18, 2009

(54) CRACKING 1-ETHERS OVER UNMODIFIED γ-ALUMINA

(75) Inventors: Xiaoliang Gao, Calgary (CA); Andrzej Krzywicki, Calgary (CA); Stacy David Ross Johnston, Calgary (CA); Alexandra Kalivoda, Calgary (CA)

(73) Assignee: Nova Chemicals (International) S.A. (CH)

( * ) Notice: Subject to any disclaimer, the term of this patent is extended or adjusted under 35 U.S.C. 154(b) by 168 days.

(21) Appl. No.: 11/709,012

(22) Filed: Feb. 21, 2007

(65) Prior Publication Data

US 2007/0203381 A1 Aug. 30, 2007

(30) Foreign Application Priority Data

Feb. 28, 2006 (CA) ................................... 2538206

(51) Int. Cl.
*C07C 1/00* (2006.01)
(52) U.S. Cl. ........................................ 585/640; 585/639
(58) Field of Classification Search ................. 585/639, 585/640, 648, 653
See application file for complete search history.

(56) References Cited

U.S. PATENT DOCUMENTS 4,234,752 A 11/1980 Wu et al.

2003/0065233 A1 4/2003 Fuji et al.

FOREIGN PATENT DOCUMENTS

| CA | 2097297 | 11/2000 |
| DE | 39 15 493 C2 | 5/1992 |
| WO | WO 2004/052809 A1 | 6/2004 |
| WO | WO 2004/078336 A2 | 9/2004 |

OTHER PUBLICATIONS

Pines, Herman & Pillai, C.N., Alumina: Catalyst and Support. XIa Modification of Alumina . . . ,JACS., 1961 vol. 83(15), pp. 3270-3274, Dept. of Chem., Northwestrern University.
Pines, Herman & Pillai, C.N., Dehydration of Alcohols over Alumina Modified by Ammonia 1,2, JACS., 1960, vol. 82(9), pp. 2401-2402, Dept. of Chem., Northwestern University.
Pines, Herman & Haag, Werner O., Alumina: Catalyst and Support. I. Alumina, its Intrinsic Acidity . . . , JACS., 1960, vol. 82, pp. 2471-2482, Dept. of Chem. Northwestern Univ.
Pines, Herman & Haag, Werner O., Alumina: Catalyst and Support. IX.1 The Alumina Catalyzed Dehydration of . . . , JACS, 1961, vol. 83, pp. 2847-2852, Dept. of Chem, Northwestern Univ.

*Primary Examiner*—In Suk Bullock
(74) *Attorney, Agent, or Firm*—Kenneth H Johnson

(57) ABSTRACT

1-Ethers may be cracked over untreated γ-alumina having a pore volume of more than 1.0 cc/g and an average pore diameter of more than 150 angstroms (Å) at a temperature from 250 to 350° C. and a pressure from 10 to 200 kPa at high conversions and good selectivity to produce the corresponding 1-alkene. The process is particularly useful to produce 1-octene from 1-methoxyoctane.

12 Claims, No Drawings able to the process it is not critical in the present invention.
CRACKING 1-ETHERS OVER UNMODIFIED γ-ALUMINA

FIELD OF THE INVENTION

The present invention relates to the cracking of lower (e.g. $C_{1-4}$) ethers of medium length (e.g. $C_{6-10}$) straight chain alkyl radicals over γ-alumina. More particularly the present invention relates to such cracking without doping the γ-alumina and in the absence of a carrier gas.

BACKGROUND OF THE INVENTION

There are a number of technologies for producing alcohols, acids and $C_{1-4}$ alkyl ethers of $C_{6-10}$ alkanes from butadiene Dow, Shell, Kuraray and Oxeno have all been developing such process for a number of years.

There are a number of papers in the name of Pines dealing with the cracking of alcohols to alkenes over alumina. A desired product was an alpha olefin and the olefin tended to undergo internal isomerization to product a mixture of products including lower amounts of the alpha olefin and higher amounts of the internal olefin. Pines discovered that doping the alumina with a base tended to reduce the amount of isomerization leading to internal olefins. (Herman Pines and C. N. Pillai, JACS., 1961, 83 (15) 3270-3274; Herman Pines and C. N. Pillai, JACS., 1960, 82 (9) 2401-2402; Herman Pines and Werner O. Haag, JACS., 1960, 2471-2482; and Herman Pines and Werner O. Haag, JACS., 1961, 2847-2852. This art teaches away from the subject matter of the present invention as it requires the alumina be doped with small amounts an alkali or alkaline earth metal.

DE 3 915 493 issued to Metalgesellschaft A. G., and Godrej Sops Ltd., India teaches cracking a fatty alcohol plus 300 ppm of ammonia over alumina to product a olefin. The patent teaches away from the subject matter of the present invention as it requires the presence of a base which is used as a carrier gas.

U.S. Pat. No. 4,234,752 issued Nov. 18, 1980 to Wu et al., assigned to Phillips Petroleum Company teaches cracking alcohols to olefins over alkali (KOH) treated γ-alumina. The reference teaches away from the subject matter of the present invention as it teaches the alumina has to be doped with an alkali.

Canadian Patent 2,097,297 (corresponding to WO 92/10450) issued Nov. 7, 2000 to Bohley et al., assigned to the Dow Chemicals Company discloses and claims a process for preparing 1-octene by telomerizing 1,3-butadiene in the presence of a tertiary phosphine and a telomerization catalyst to product a 1-substituted 2,7-octadiene which is subsequently hydrogenated to a 1-substituted to octane which is cracked to 1-octene over alumina which may be modified. In the only example 1 methoxyoctane is passed over γ-alumina to produce 1-octene. The conversion was 80% and the selectivity to octenes (all octenes) was 66% at 330° C. There is no teaching in the reference as to pore size of the γ-alumina. The present invention achieves a greater selectivity to octenes. The reference gives no teaching or suggestion that the 1 substituted octane conversion could be increased by selecting a γ-alumina having a selected pore size.

WO 2004/052809 published Jun. 24, 2004 in the name of Kaizik et al., assigned to Oxeno Olefinchemie GMBH discloses cracking a 1-alkyl ether of octane over an alkali doped aluminum oxide. The present invention has eliminated an essential feature of this prior art, namely the doping with an alkali.

United States Patent Application 2003/0065233 A1 published Apr. 23, 2003 in the name of Fuji et al., assigned to Kuraray Co., Ltd. teaches a process for cracking a primary alcohol or ether to a 1-olefin in the presence of an alumina catalyst and an amine. The present invention has eliminated the required amine of the reference.

WO 2004/078336 A2 published Sep. 16, 2004 in the name of Ziehe et al., assigned to Sasol Germany GMBH teaches cracking (dehydration) a 1-alcohol to an alpha olefin over a γ-alumina having a pore volume greater than 0.9 cc/g, and a bimodal pore radii distribution such that there is at least one maximum in the mesopore size in the range from 30 to 80 Å (0.003 to 0.008 microns or micrometers) and one maximum in the macropore range greater than 1,000 Å (0.1 microns or micrometers) and the macropores make up more than 40% of the total pore volume. Preferably the alcohol is passed over the catalyst together with a carrier gas. The reference does not teach or suggest the process could be used with an ether. The present invention has eliminated the carrier gas. Further the present invention is directed to alumina having a pore volume not less than 1.1 cc/g.

The present invention seeks to provide a simple process for cracking lower ethers of $C_{6-10}$ alkanes to $1-C_{6-10}$ olefins at a conversion not less than 70% and a WHSV from 8 to 20 $hr^{-1}$ in the presence of a γ-alumina which has not been treated with a base and has a pore volume of at least 1.0 cc/g, preferably 1.1 cc/g and an average pore diameter of greater than 150 Å, preferably greater than 190 Å and most preferably more than 200 Å.

SUMMARY OF THE INVENTION

The present invention provides a process comprising passing a feed stream comprising not less than 90 weight % of a $C_{1-4}$ ether of a $C_{6-10}$ alkane, in the absence of a sweep gas over γ alumina having a pore volume of not less than 1.0 cc/g, preferably not less than 1.1 cc/g and an average pore diameter of more than 150 Å, which alumina has not been modified with a base at a WHSV from 8 to 20 $hr^{-1}$, a temperature from 250° C. to 350° C., a pressure from 10 kPa to 200 kPa to produce the corresponding 1-alkene at a selectivity of not less than 90% and a conversion of the starting ether of not less than 50%.

BEST MODE

The feed stream useful with the present invention comprises 90 weight % of a $C_{1-4}$ ether of a $C_{6-10}$ alkane. Preferably the ether is a $C_{1-2}$ ether of a $C_{6-8}$ alkane. Typically the ether would be a hexane or octane methyl or ethyl ether, preferably methyl octane ether (MOAN). Generally the ether is passed through the alumina bed of the present invention in the form of a gas, in the absence of a carrier gas. To do this the ether is heated to its vaporization temperature and then passed through the catalyst bed at reaction temperature. The feedstock is passed through the alumina bed to provide a WHSV (weight hourly space velocity) from 8 to 20 $h^{-1}$, typically from 10 to 18 $hr^{-1}$.

The feedstock may be obtained by the above noted telomerization processes for diolefins and subsequent hydrogenation of the resulting functionalized diene to an alkane. In accordance with the present invention the functionalization is an ether. However, for the telomerization process the product could contain other functional groups such as alcohols or acids which could readily be converted to ethers.

The γ-alumina used in the present invention has a cumulative pore volume of not less than 1.0 cc/g, preferably greater than 1.1 cc/g. The cumulative pore volume and pore size distribution of the γ-alumina may be determined using known techniques such as inert gas desorption isotherm. One method is described in ASTM D 4641-94. The preferred inert gas for the measurement is nitrogen. An alternate method is by mercury intrusion under vacuum at various pressures.

Generally the average pore diameter will be not less than 150 Å preferably larger than 190 Å, more preferably larger than 200 Å.

The γ-alumina catalyst is typically in the form of granules, extrudrates, or pellets having a size from about 0.3 mm to about 1.5 cm.

The starting ether is heated to form a gas. The resulting gas is then passed through a bed of the above noted alumina catalyst. The gas may be at pressures from 10.0 kPa to 200 kPa, preferably from 10.0 kPa to 100 kPa. The gas needs to be kept in the form of a vapor and the process may be conducted at temperatures from 280° C. to 330° C., preferably from 290° C. to 320° C.

The product stream comprises the 1-olefin, the alcohol resulting from cracking (cleavage) of the ether, and minor amounts of by products such as higher alcohols (e.g. hexanol or octanol). The conversion of the starting ether should be greater than 50%, preferably greater than 60%, most preferably greater than 65%. The selectivity for the 1-olefin should be greater than 90%, preferably greater than 95% most preferably greater than 97%.

The resulting product stream is in vapour form. Products may be separated using conventional distillation techniques. The bulk of the product stream will be the 1-olefin and the alcohol resulting from the cleavage of the ether.

Preferably the starting ether is methyl octyl ether (1-methoxyoctane—"MOAN") or methyl hexyl ether (1-methoxyhexane) and the resulting olefins would be 1-octene and 1-hexene respectively with methanol being the alcohol resulting from the cleavage of the ether. While it may be possible to concurrently treat different ethers to yield a mixed stream of olefins this would increase the distillation process after the cracking reaction.

The present invention will now be illustrated by the following non limiting examples.

EXAMPLES

Examples 1-4

All "cracking" reactions were performed in a fixed bed tubular reactor. There are two separate heating zones in the system. The first zone, 4" in length, is controlled at about 300° C. to vaporize the feed liquid and to maintain the vapor temperature close to the reaction temperature. The second reaction zone has dimensions of 0.402" ID×2". Both zones are controlled by independent thermocouples and temperature-control units. A catalyst was loaded in the reactor, which was heated at 300° C. overnight under a slow stream of nitrogen. The ether "MOAN" was fed into the reactor at the top with a syringe pump. The product stream was passed through a water cooled condenser and the liquid was collected for analysis by gas chromatography (Agilent 6890N). Under normal circumstances, the MOAN was fed at a given WHSV for 0.5 hr before the first sample was collected. After sampling, if a change of WHSV or reaction temperature was needed, the reactor was stabilized again for another 0.5 hr before the next sample was collected. In the process, no sweep gas was required. Vaporization of the fed MOAN pushes the products through the catalyst bed and the reactor.

The results are collected in Tables 1-4. Good conversion of the feed (C %) and selectivity to octenes ($S_{C8s}$ %) were achieved with all the catalysts. However, the critical parameter, selectivity to 1-octene ($S_{C8\text{-}1}$ %), depends on the different types of alumina. It appears that the selectivity to 1-octene increases in the order of γ-Alumina (total pore volume 0.55-0.75 cm$^3$/g, average pore diameter 110 Å)<γ-Alumina (total pore volume 0.8 cm$^3$/g, average pore diameter 136 Å)<γ-Alumina (total pore volume 1.1 cm$^3$/g, pore diameter 196 Å)~=γ-Alumina (total pore volume 1.2 cm$^3$/g, average pore diameter 221 Å), which follows the same trend as the total pore volumes or pore diameters of the catalysts:

In the tables the production of several by-products is noted particularly dioctyl ether, dimethyl ether, methanol and octanol.

The catalyst properties are set forth in the following table.

| Catalyst | Form | Diameter | Pore Volume cc/g | Surface Area m$^2$/g | Average Pore Diameter Angstroms |
|---|---|---|---|---|---|
| A | Extrudate | 1.5-7 mm | 0.55-0.76 | 200 | 110 |
| B | Extrudate | 1.59 mm | 0.8 | 235 | 136 |
| C | Spheres | 4-8 mesh | 1.1 | 225 | 196 |
| D | Extrudate | 1.8 mm | 1.2 | 217 | 221 |

Note:
4-8 mesh gives a size from 4.75 to 2.36 mm.

TABLE 1

Catalytic Cracking MOAN to 1-Octene with Catalyst A

| Run # | TOS (hr) | Sample | Temp. (° C.) | WHSV (h$^{-1}$) | Flow (ml/hr) | C (%) | $S_{C8s}$ (%) | $S_{C8\text{-}1}$ (%) | (n-octyl)$_2$O | MeOMe | MeOH | n-octanol |
|---|---|---|---|---|---|---|---|---|---|---|---|---|
| 1 | 0.75 | A | 300 | 10.0 | 16.3 | 100.00 | 97.54 | 31.60 | 0.00 | 2.51 | 0.14 | 0.01 |
|   | 1.5 | B | 300 | 10.0 | 16.3 | 100.00 | 97.29 | 42.42 | 0.01 | 2.30 | 0.14 | 0.01 |
|   | 2.5 | C | 300 | 10.0 | 16.3 | 100.00 | 97.50 | 51.72 | 0.00 | 2.33 | 0.13 | 0.00 |
|   | 3.5 | D | 300 | 10.0 | 16.3 | 100.00 | 97.34 | 59.58 | 0.01 | 2.63 | 0.15 | 0.02 |
|   | 5 | E | 300 | 10.0 | 16.3 | 100.00 | 96.87 | 68.35 | 0.01 | 2.10 | 0.13 | 0.09 |
|   | 6.25 | F | 300 | 10.0 | 16.3 | 98.45 | 97.32 | 76.62 | 0.02 | 2.46 | 0.18 | 0.24 |
| 2 | 7.5 | A | 300 | 10.0 | 16.3 | 99.11 | 97.39 | 75.56 | 0.01 | 2.57 | 0.18 | 0.13 |
|   | 8.5 | B | 300 | 10.0 | 16.3 | 98.00 | 96.82 | 83.26 | 0.03 | 2.12 | 0.15 | 0.31 |
|   | 9.25 | C | 300 | 10.0 | 16.3 | 97.70 | 97.15 | 86.91 | 0.04 | 2.33 | 0.17 | 0.38 |
|   | 10.5 | D | 300 | 10.0 | 16.3 | 97.33 | 97.01 | 90.40 | 0.05 | 2.50 | 0.19 | 0.46 |
|   | 12 | E | 300 | 10.0 | 16.3 | 97.35 | 96.97 | 91.73 | 0.05 | 2.57 | 0.21 | 0.48 |
|   | 13.25 | F | 300 | 10.0 | 16.3 | 97.48 | 97.01 | 91.89 | 0.04 | 2.36 | 0.20 | 0.47 |
| 3 | 15.25 | A | 300 | 10.0 | 16.3 | 98.19 | 97.00 | 90.45 | 0.02 | 2.47 | 0.17 | 0.33 |

TABLE 1-continued

Catalytic Cracking MOAN to 1-Octene with Catalyst A

| Run # | TOS (hr) | Sample | Temp. (°C.) | WHSV (h$^{-1}$) | Flow (ml/hr) | C (%) | $S_{C8s}$ (%) | $S_{C8-1}$ (%) | (n-octyl)$_2$O | MeOMe | MeOH | n-octanol |
|---|---|---|---|---|---|---|---|---|---|---|---|---|
|   | 16.5 | B | 300 | 10.0 | 16.3 | 97.52 | 96.97 | 91.61 | 0.04 | 1.63 | 0.13 | 0.46 |
|   | 18.5 | C | 300 | 10.0 | 16.3 | 97.05 | 96.85 | 92.18 | 0.05 | 2.65 | 0.20 | 0.54 |
|   | 19.5 | D | 300 | 10.0 | 16.3 | 96.26 | 96.78 | 92.57 | 0.08 | 2.66 | 0.22 | 0.65 |
|   | 20.5 | E | 300 | 10.0 | 16.3 | 96.00 | 96.70 | 92.68 | 0.08 | 2.14 | 0.19 | 0.71 |
| 4 |      | A | 300 | 10.0 | 16.3 | 98.15 | 96.20 | 88.43 | 0.02 | 2.68 | 0.19 | 0.30 |
|   |      | B | 300 | 12.0 | 19.6 | 95.64 | 96.88 | 91.95 | 0.08 | 3.61 | 0.25 | 0.67 |
|   |      | C | 300 | 12.0 | 19.6 | 95.35 | 96.73 | 92.90 | 0.11 | 3.08 | 0.28 | 0.80 |
|   |      | D | 300 | 14.0 | 22.9 | 92.82 | 96.88 | 93.64 | 0.23 | 2.21 | 0.29 | 1.11 |
|   |      | E | 300 | 16.0 | 26.2 | 90.54 | 95.85 | 94.27 | 0.29 | 4.39 | 0.41 | 1.43 |
|   |      | F | 300 | 18.0 | 29.4 | 88.88 | 95.34 | 94.55 | 0.42 | 2.69 | 0.33 | 1.71 |

TABLE 2

Catalytic Cracking MOAN to 1-Octene with Catalyst B

| Run # | TOS (hr) | Sample | Temp (°C.) | WHSV (h$^{-1}$) | LHSV (h$^{-1}$) | Flow (ml/hr) | C (%) | $S_{C8s}$ (%) | $S_{C8-1}$ (%) | (n-octyl)$_2$O | MeOMe | MeOH | n-octanol |
|---|---|---|---|---|---|---|---|---|---|---|---|---|---|
| 5 | 1 | A | 300 | 10.0 | 6.4 | 13.5 | 99.96 | 97.85 | 63.04 | 0.00 | 2.27 | 0.14 | 0.01 |
|   | 3 | B | 300 | 10.0 | 6.4 | 13.5 | 98.78 | 97.50 | 82.31 | 0.02 | 2.49 | 0.16 | 0.20 |
|   | 4.5 | C | 300 | 10.0 | 6.4 | 13.5 | 95.83 | 96.87 | 91.89 | 0.10 | 2.24 | 0.19 | 0.74 |
|   | 5.5 | D | 300 | 10.0 | 6.4 | 13.5 | 94.72 | 96.56 | 93.97 | 0.15 | 2.67 | 0.23 | 0.97 |
| 6 | 6.5 | A | 300 | 10.0 | 6.4 | 13.5 | 96.18 | 96.98 | 92.74 | 0.07 | 2.77 | 0.22 | 0.65 |
|   | 8 | B | 300 | 10.0 | 6.4 | 13.5 | 93.97 | 96.49 | 94.34 | 0.17 | 2.66 | 0.25 | 1.05 |
|   | 9.5 | C | 300 | 10.0 | 6.4 | 13.5 | 92.84 | 96.19 | 94.81 | 0.23 | 2.66 | 0.28 | 1.25 |
|   | 11 | D | 300 | 10.0 | 6.4 | 13.5 | 92.41 | 96.11 | 94.67 | 0.25 | 2.79 | 0.29 | 1.30 |
|   | 12.5 | E | 300 | 10.0 | 6.4 | 13.5 | 91.06 | 95.90 | 94.58 | 0.32 | 2.65 | 0.30 | 1.48 |
| 7 | 14.5 | A | 300 | 10.0 | 6.4 | 13.5 | 95.64 | 96.87 | 93.72 | 0.09 | 2.62 | 0.22 | 0.77 |
|   | 16 | B | 300 | 10.0 | 6.4 | 13.5 | 94.25 | 96.52 | 94.61 | 0.16 | 2.60 | 0.25 | 1.04 |
|   | 18.5 | C | 300 | 10.0 | 6.4 | 13.5 | 92.46 | 96.16 | 94.98 | 0.25 | 2.24 | 0.27 | 1.31 |
|   | 21 | D | 300 | 10.0 | 6.4 | 13.5 | 89.85 | 95.56 | 95.12 | 0.42 | 2.86 | 0.34 | 1.70 |
| 8 |   | A | 300 | 10.0 | 6.4 | 13.5 | 94.83 | 96.40 | 94.22 | 0.14 | 2.29 | 0.21 | 0.92 |
|   |   | B | 300 | 12.0 | 7.6 | 16.2 | 92.50 | 96.16 | 94.77 | 0.25 | 3.11 | 0.28 | 1.24 |
|   |   | C | 300 | 14.0 | 8.9 | 18.9 | 88.35 | 95.18 | 95.66 | 0.53 | 2.72 | 0.34 | 1.90 |
|   |   | D | 300 | 16.0 | 10.2 | 21.6 | 86.79 | 94.69 | 95.91 | 0.70 | 3.31 | 0.41 | 2.14 |
|   |   | E | 300 | 18.0 | 11.4 | 24.3 | 85.70 | 94.47 | 95.95 | 0.76 | 3.32 | 0.43 | 2.30 |

TABLE 3

Catalytic Cracking MOAN to 1-Octene with Catalyst C

| Run # | TOS (hr) | Sample | Temp (°C.) | WHSV (h$^{-1}$) | LHSV (h$^{-1}$) | Flow (ml/hr) | C (%) | $S_{C8s}$ (%) | $S_{C8-1}$ (%) | (n-octyl)$_2$O | MeOMe | MeOH | n-octanol |
|---|---|---|---|---|---|---|---|---|---|---|---|---|---|
| 9 | 1.5 | A | 300 | 10 | 6.4 | 15.5 | 100.00 | 97.27 | 42.86 | 0.01 | 6.15 | 0.45 | 0.00 |
|   | 3 | B | 300 | 10 | 6.4 | 15.5 | 100.00 | 97.47 | 61.85 | 0.01 | 6.46 | 0.53 | 0.00 |
|   | 4.5 | C | 300 | 10 | 6.4 | 15.5 | 99.94 | 97.43 | 80.20 | 0.01 | 5.91 | 0.45 | 0.01 |
|   | 6 | D | 300 | 10 | 6.4 | 15.5 | 97.70 | 97.15 | 92.89 | 0.02 | 6.85 | 0.62 | 0.26 |
| 10 | 7.5 | A | 300 | 10 | 6.4 | 15.5 | 97.62 | 97.07 | 93.50 | 0.03 | 9.80 | 0.91 | 0.30 |
|   | 9 | B | 300 | 10 | 6.4 | 15.5 | 96.20 | 96.82 | 94.26 | 0.06 | 9.55 | 1.00 | 0.48 |
|   | 10.5 | C | 300 | 10 | 6.4 | 15.5 | 94.17 | 96.53 | 94.72 | 0.13 | 8.96 | 1.10 | 0.70 |
|   | 12 | D | 300 | 10 | 6.4 | 15.5 | 95.59 | 96.78 | 94.53 | 0.08 | 7.38 | 0.83 | 0.60 |
| 11 | 13.5 | A | 300 | 10 | 6.4 | 15.5 | 95.50 | 96.77 | 94.51 | 0.08 | 6.69 | 0.83 | 0.62 |
|   | 15 | B | 300 | 10 | 6.4 | 15.5 | 95.00 | 96.54 | 94.56 | 0.10 | 10.81 | 1.26 | 0.63 |
|   | 16.5 | C | 300 | 10 | 6.4 | 15.5 | 94.86 | 96.80 | 94.71 | 0.10 | 5.57 | 0.71 | 0.72 |
|   | 19 | D | 300 | 10 | 6.4 | 15.5 | #REF! | #REF! | #REF | #REF! | #REF! | #REF! | #REF! |
| 12 | 20.5 | A | 300 | 10 | 6.4 | 15.5 | 95.76 | 96.92 | 94.32 | 0.08 | 7.05 | 0.74 | 0.57 |
|   |   | B | 300 | 12 | 7.6 | 18.6 | 93.48 | 96.55 | 95.14 | 0.14 | 10.03 | 1.31 | 0.83 |
|   |   | C | 300 | 14 | 8.9 | 21.8 | 91.46 | 96.11 | 95.49 | 0.22 | 7.18 | 1.10 | 1.10 |
|   |   | D | 300 | 16 | 10.2 | 24.9 | 89.67 | 95.82 | 95.70 | 0.26 | 9.91 | 1.56 | 1.12 |
|   |   | E | 300 | 18 | 11.4 | 28 | 85.92 | 95.03 | 96.03 | 0.44 | 9.84 | 1.71 | 1.44 |

TABLE 4

Catalytic Cracking MOAN to 1-Octene with Catalyst D

| Run # | TOS (hr) | Sample | Temp (° C.) | WHSV (h$^{-1}$) | Flow (ml/hr) | C (%) | S$_{C8s}$ (%) | S$_{C8-1}$ (%) | (n-octyl)$_2$O | MeOMe | MeOH | n-octanol |
|---|---|---|---|---|---|---|---|---|---|---|---|---|
| 13 | 1 | A | 300 | 10.0 | 13.8 | 99.93 | 97.79 | 75.05 | 0.00 | 3.02 | 0.14 | 0.01 |
|  | 2.2 | B | 300 | 10.0 | 13.8 | 97.80 | 97.28 | 88.10 | 0.02 | 3.10 | 0.18 | 0.32 |
|  | 3.5 | C | 300 | 10.0 | 13.8 | 89.15 | 95.58 | 95.11 | 0.39 | 2.29 | 0.30 | 1.72 |
|  | 4.75 | D | 300 | 10.0 | 13.8 | 87.91 | 95.06 | 95.58 | 0.57 | 4.57 | 0.50 | 2.00 |
|  | 6 | E | 300 | 10.0 | 13.8 | 86.59 | 94.77 | 95.74 | 0.69 | 3.13 | 0.38 | 2.21 |
|  | 7 | F | 300 | 10.0 | 13.8 | 86.79 | 94.82 | 95.75 | 0.68 | 2.77 | 0.36 | 2.19 |
| 14 | 1 | A | 300 | 10.0 | 13.8 |  |  |  |  |  |  |  |
|  | 2.2 | B | 300 | 10.0 | 13.8 | 83.81 | 94.10 | 95.96 | 1.00 | 2.05 | 0.36 | 2.62 |
|  | 3 | C | 300 | 12.0 | 16.6 | 82.40 | 93.85 | 96.29 | 1.06 | 1.21 | 0.33 | 2.84 |
|  | 4 | D | 300 | 14.0 | 19.3 | 76.54 | 92.20 | 96.86 | 1.70 | 4.36 | 0.66 | 3.66 |
|  | 5 | E | 300 | 16.0 | 22 | 75.65 | 92.07 | 96.98 | 1.71 | 4.64 | 0.70 | 3.74 |
|  | 6 | F | 300 | 18.0 | 24.8 | 73.23 | 91.57 | 97.14 | 1.89 | 4.90 | 0.78 | 4.02 |
|  | 7.5 | G | 300 | 18.0 | 24.8 | 74.18 | 91.88 | 97.02 | 1.74 | 4.13 | 0.74 | 3.87 |
| 15 |  | A | 300 | 10.0 | 13.8 | 93.91 | 96.36 | 93.15 | 0.11 | 2.49 | 0.23 | 0.95 |
|  |  | B | 295 | 10.0 | 13.8 | 78.55 | 93.13 | 96.29 | 1.27 | 3.17 | 0.60 | 3.20 |
|  |  | C | 290 | 10.0 | 13.8 | 63.06 | 87.26 | 97.35 | 4.52 | 3.38 | 0.87 | 5.58 |
|  |  | D | 285 | 10.0 | 13.8 | 54.25 | 83.05 | 97.74 | 7.14 | 3.32 | 1.00 | 6.92 |
|  |  | E | 280 | 10.0 | 13.8 | 44.47 | 77.39 | 98.10 | 11.04 | 3.21 | 1.16 | 8.32 |

Note:
for run 14 sample A there was a problem with the Gas Chromatograph so the run was terminated.

What is claimed is:

1. A process comprising passing a feed stream comprising not less than 90 weight % of a C$_{1-4}$ ether of a C$_{6-10}$ alkane, in the absence of a sweep gas and the absence of an amine, over γ alumina having a pore volume of not less than 1.0 cc/g and an average pore diameter of more than 150 Å, which alumina has not been modified with a base at a WHSV from 8 to 20 hr$^{-1}$, a temperature from 250° C. to 350° C., a pressure from 10 kPa to 200 kPa to produce the corresponding 1-alkene at a selectivity of not less than 90%, and a conversion of the starting ether of not less than 50%.

2. The process according to claim 1, wherein the pore volume of the γ-alumina is not less than 1.1 cc/g and an average pore diameter of more than 190 Å.

3. The process according to claim 2, wherein the temperature is from 280° C. to 330° C.

4. The process according to claim 3, wherein the pressure is from 10 kPa to 200 kPa.

5. The process according to claim 4, the alkane is a C$_{6-8}$ alkane.

6. The process according to claim 5, wherein the ether is a C$_{1-2}$ alkyl ether.

7. The process according to claim 6, wherein the temperature is from 290° C. to 320° C.

8. The process according to claim 7, wherein the pressure is from 10 kPa to 100 kPa.

9. The process according to claim 8, wherein the selectivity to the corresponding 1-alkene is greater than 95%.

10. The process according to claim 9, wherein the conversion of the starting ether is not less than 65%.

11. The process according to claim 10 wherein the average pore diameter is greater than 200 Å.

12. The process according to claim 11, wherein the starting ether is methyl octyl ether and the corresponding 1-alkene is 1-octene.

* * * * *